United States Patent
Baker et al.

[11] Patent Number: 5,261,904
[45] Date of Patent: Nov. 16, 1993

[54] LASER CATHETER HAVING DIFFRACTION GRATING FOR BEAM SHAPING

[75] Inventors: Glenn S. Baker, Wakefield; Edward L. Sinofsky, Peabody, both of Mass.

[73] Assignee: C. R. Bard, Inc., Murray Hill, N.J.

[21] Appl. No.: 765,398

[22] Filed: Sep. 24, 1991

Related U.S. Application Data

[63] Continuation of Ser. No. 472,354, Jan. 30, 1990, abandoned.

[51] Int. Cl.$^5$ .............................................. A61B 5/06
[52] U.S. Cl. ........................................... 606/17; 606/7; 606/15
[58] Field of Search ............... 128/395, 397, 398; 606/2-4, 6-18

[56] References Cited

U.S. PATENT DOCUMENTS

| | | | |
|---|---|---|---|
| 3,188,188 | 6/1965 | Norton | 350/96.24 |
| 4,648,892 | 3/1987 | Kittrell et al. | 606/15 |
| 4,672,961 | 6/1987 | Davies | 606/18 |
| 4,718,417 | 1/1988 | Kittrell et al. | 128/303.1 |
| 4,917,084 | 4/1990 | Sinofsky | 606/3 |
| 4,950,266 | 8/1990 | Sinofsky | 606/7 |

Primary Examiner—David M. Shay
Attorney, Agent, or Firm—Wolf, Greenfield & Sacks

[57] ABSTRACT

A laser catheter includes an elongated tubular catheter body, one or more optical fibers extending through the catheter body and a catheter window mounted at the distal end of the catheter body. The optical fibers direct laser energy through the catheter window for removal of biological material. A diffraction grating is formed on the proximal surface of the catheter window in alignment with laser energy from the optical fibers. The laser energy is modified by the diffraction grating to provide a desired spatial distribution pattern. Preferably, the diffraction grating provides a diverging beam suitable for forming a hole in an obstruction, the hole having a diameter that is approximately the same as the diameter of the catheter. The diffraction grating enables formation at the distal end of the catheter of a beam pattern having an elliptical or other noncircular cross section. In another embodiment, an optical fiber with a noncircular cross section is used to shape the laser radiation emitted from the laser catheter.

13 Claims, 6 Drawing Sheets

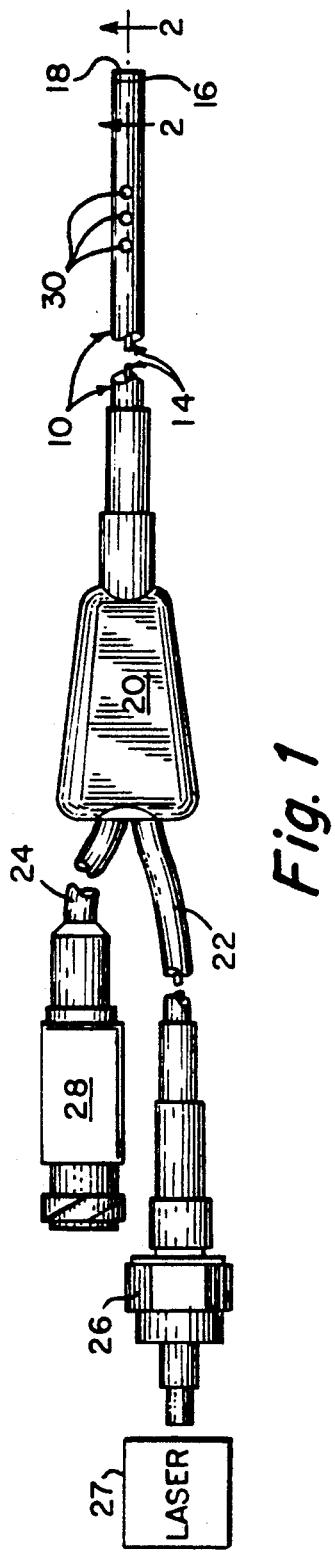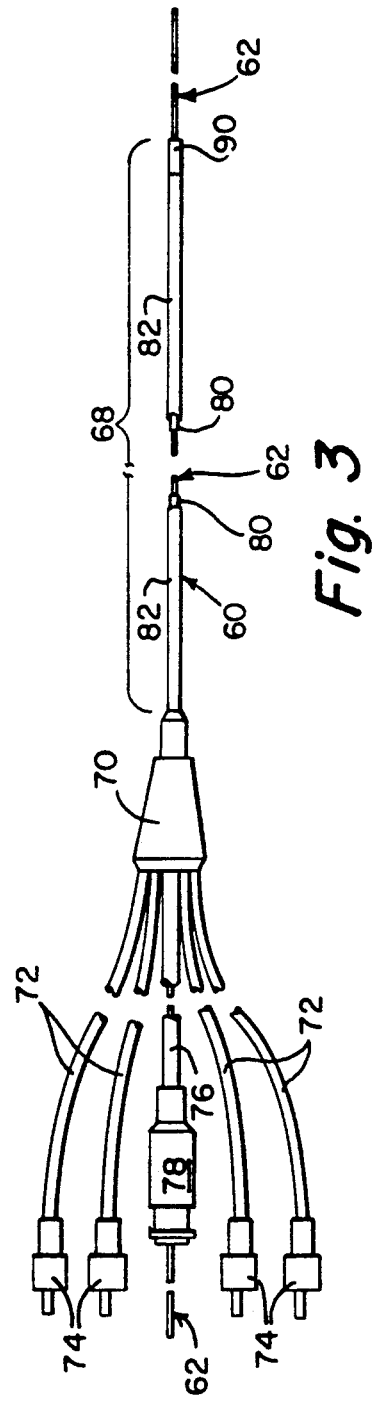

LASER CATHETER HAVING DIFFRACTION GRATING FOR BEAM SHAPING

This application is a continuation of application Ser. No. 07/472,354, filed Jan. 30, 1990, now abandoned.

FIELD OF THE INVENTION

This invention relates to catheters for controlled removal of plaque and other biological obstructions with radiant energy and, more particularly, to catheters which utilize means such as a diffraction grating for shaping a beam of radiant energy.

BACKGROUND OF THE INVENTION

A number of nonsurgical techniques for treatment of obstructed blood vessels have been investigated. Such techniques include balloon angioplasty wherein a passage is formed in the obstructed region with a dilatation balloon, laser balloon angioplasty wherein heat and pressure are simultaneously applied to enlarge a passage through a blood vessel, and the so-called "hot tip" technique wherein a high temperature heating element is pushed through plaque deposits to form a passage. Another widely investigated technique involves the use of radiant energy, typically laser energy, to remove obstructions such as plaque deposits by vaporization or ablation. The laser removal technique employs a catheter having one or more optical fibers extending through the catheter to its distal end. The catheter is advanced through a blood vessel to an obstructed site, and laser energy of a suitable wavelength and intensity to remove the deposit is directed through the optical fiber or fibers. Catheters for removal of obstructions with laser energy are disclosed in U.S. Pat. No. 4,817,701 issued Apr. 4, 1989 to Roth et al and U.S. Pat. No. 4,850,351 issued Jul. 25, 1989 to Herman et al.

A catheter for controlled removal of obstructions with laser energy must meet a number of important requirements. The catheter must be small in diameter and highly flexible so that it can be advanced to obstructions in small diameter vessels. It is frequently desired that the catheter be used with a guidewire which assists in positioning the catheter. In this case, the catheter must be specially adapted for use with a guidewire. The laser energy directed through the optical fiber or fibers must have sufficient intensity to remove the plaque deposits but must be controlled in a manner which eliminates the possibility of perforating the blood vessel wall with the laser energy. Vessel perforation may be prevented by controlling the laser energy pattern such that high intensity occurs only in a shallow working region just beyond the distal tip of the catheter.

It is usually desired that the laser energy form a hole in the obstruction of sufficient diameter to pass the catheter (approximately 1.5 mm). The catheter is advanced through the hole which it forms, and laser energy is repeatedly applied so as to form a passage through a long obstruction. It is customary to launch a laser beam into the proximal end of the optical fiber in a laser catheter with low divergence in order to provide good transmission through the fiber and to reduce bending losses in the fiber. However, the low divergence input laser beam results in the laser energy being emitted from the distal end of the optical fiber with a small angle of divergence, typically on the order of about 6°. A small divergence laser beam passing through an optical fiber having a diameter on the order of 200 micrometers does not form a hole of sufficient diameter to pass the catheter without modification of the laser beam.

A hole approximately the diameter of the catheter can be obtained by expanding the laser beam which exits from the optical fiber with a lens arrangement and/or by utilizing multiple optical fibers. However, as the number of optical fibers is increased, the flexibility of the catheter decreases. Lens arrangements can, in theory, be utilized to expand the laser beam or beams. The aforementioned U.S. Pat. No. 4,817,601 discloses a laser catheter having a lens arrangement for providing a desired laser radiation pattern. However, in practice, lens assemblies of sufficiently small size to be used in a coronary angioplasty catheter are difficult to fabricate, particularly when multiple, small-diameter optical fibers are utilized. A lens assembly must be able to withstand the high laser energy levels required for removal of obstructions. Another approach to beam expansion is disclosed in the aforementioned U.S. Pat. No. 4,850,351. A window having sufficient thickness to permit the laser beams to diverge before emerging from the distal tip of the catheter is mounted at the distal end of the catheter. However, such a window reduces the flexibility of the tip region of the catheter.

Various other lens arrangements have been disclosed in the prior art. U.S. Pat. No. 4,800,876 issued Jan. 31, 1989 to Fox et al discloses a laser catheter for angioplasty including multiple optical fibers and a lens arrangement at the distal end of each optical fiber. A converging lens focuses the laser beam and prevents divergence toward the lumen wall, and a prism bends the laser beam toward the center of the lumen. U.S. Pat. No. 4,273,109 issued Jun. 16, 1981 to Enderby discloses an endoscope wherein light is transmitted through an optical fiber that is terminated in a lens system which can have either a converging or diverging characteristic. U.S. Pat. No. 4,266,534 issued May 12, 1981 to Ogawa discloses an illumination unit for an endoscope wherein a window covers the distal end of an optical fiber. The window includes spherical lens portions having different radii to provide a uniform illumination pattern. A collimator lens for an optical fiber including a fresnel lens pattern formed on a cylindrical member is disclosed in U.S. Pat. No. 4,815,807 issued Mar. 28, 1989 to Kaneko et al. An interlaced binary diffraction grating for laser beam profile shaping is disclosed by W. B. Veldkamp, *Applied Optics,* Vol. 21, No. 17, September 1982, pp. 3209-3212.

It is a general object of the present invention to provide improved catheters for controlled removal of biological obstructions with radiant energy.

It is another object of the present invention to provide a catheter having a diffraction grating at the distal end of an optical fiber to control the spatial distribution pattern of radiant energy emitted from the catheter.

It is a further object of the present invention to provide a catheter for removing biological obstructions with radiant energy, the radiant energy having a spatial distribution which reduces or eliminates the possibility of vessel wall perforation.

It is still another object of the present invention to provide a catheter which is small in diameter and highly flexible.

It is yet another object of the present invention to provide a catheter which is low in cost and easy to manufacture.

It is still another object of the present invention to provide a catheter having a working region wherein tissue is removed by radiant energy, the working region having a short axial depth and a diameter approximately equal to the diameter of the catheter.

It is a further object of the invention to provide an improved laser catheter for use in transluminal angioplasty.

It is another object of the present invention to provide a catheter including at least one optical fiber and means for modifying the spatial distribution pattern of laser radiation emitted from the optical fiber.

SUMMARY OF THE INVENTION

According to the present invention, these and other objects and advantages are achieved in a catheter for removing biological material with radiant energy, typically laser energy. The catheter comprises elongated catheter means having a proximal end and a distal end, optical fiber means extending through the catheter means from the proximal end to the distal end, the optical fiber means having a distal tip, and transmission diffraction grating means mounted at or near the distal end of the catheter means such that radiant energy directed through the optical fiber means from the proximal end of the catheter means passes through the transmission diffraction grating means and is modified by the transmission diffraction grating means into a desired spatial distribution pattern for irradiation of biological material.

The transmission diffraction grating means preferably comprises a window having a transmission diffraction grating on a proximal surface thereof. The distal tip of the optical fiber means is spaced from the transmission diffraction grating by a material having a different refractive index from the window. Preferably, the distal tip of the optical fiber means is spaced from the transmission diffraction grating by a small air gap. In another embodiment, the transmission diffraction grating is formed on a distal end surface of the optical fiber means.

The transmission diffraction grating expands the radiant energy in at least one dimension perpendicular to an axis of the catheter means. Preferably, the transmission diffraction grating is used to provide a pattern of radiant energy having a cross-sectional dimension approximately equal in diameter to the diameter of the catheter means.

The transmission diffraction grating can comprise any of a number of known grating patterns including parallel grooves, a grid-type pattern of grooves, radial grooves or a holographic grating pattern. Preferably, the grating pattern has nonuniform groove spacing in order to provide a substantially uniform spatial distribution of energy.

The optical fiber means can comprise a single optical fiber or plural optical fibers. In a preferred embodiment, plural optical fibers are mounted circumferentially at the distal end of the catheter, and the window includes a centrally located aperture in communication with a lumen in the catheter means. A guidewire is advanced through the catheter and through the aperture in the window to assist in placement of the catheter. The transmission diffraction grating comprises plural grating sections formed on the window, one of the grating sections being aligned with each of the optical fibers.

According to a further aspect of the invention, a proximally-facing reflecting layer can be provided on the distal surface of the window. Radiant energy, after passing through the transmission diffraction grating, is reflected in a generally proximal direction to provide a desired pattern.

According to yet another aspect of the invention, the proximal surface of the window has at least one recess formed therein. A transmission diffraction grating is formed on an end wall of the recess. When an optical fiber is mounted in a fiber holder and the distal end of the optical fiber is flush with the end of the fiber holder, the transmission diffraction grating is spaced from the distal end of the optical fiber by the axial depth of the recess.

According to another aspect of the invention, there is provided a catheter for removing biological material from a body lumen with radiant energy. The catheter comprises an elongated catheter body having a proximal end and a distal end, at least one optical fiber extending through the catheter body from the proximal end to the distal end, and shaping means for modifying radiant energy directed through the optical fiber into a noncircular distribution pattern in a plane perpendicular to the catheter body. The noncircular distribution pattern is typically elongated in cross-section and may be elliptical in cross-section.

The shaping means can comprise a transmission diffraction grating mounted at or near the distal end of the catheter body such that radiant energy emitted from the optical fiber is directed through the transmission diffraction grating as described above. Alternatively, the shaping means can comprise a section of the optical fiber near the distal end of the catheter body having a noncircular cross-section. The noncircular beam cross-section is particularly useful in a laser catheter having multiple optical fibers. Laser beams with elongated cross-sections from a plurality of optical fibers can be combined to provide a desired beam pattern such as an annular beam pattern. The shaping means permits a desired beam pattern to be provided with fewer optical fibers than was possible in prior art catheters.

BRIEF DESCRIPTION OF THE DRAWINGS

For a better understanding of the present invention together with other and further objects, advantages and capabilities thereof, reference is made to the accompanying drawings which are incorporated herein by reference and in which:

FIG. 1 illustrates a single optical fiber laser catheter in accordance with the invention;

FIG. 3 illustrates a multiple optical fiber wire-guided laser catheter in accordance with the invention;

DETAILED DESCRIPTION OF THE INVENTION

Figure 2:
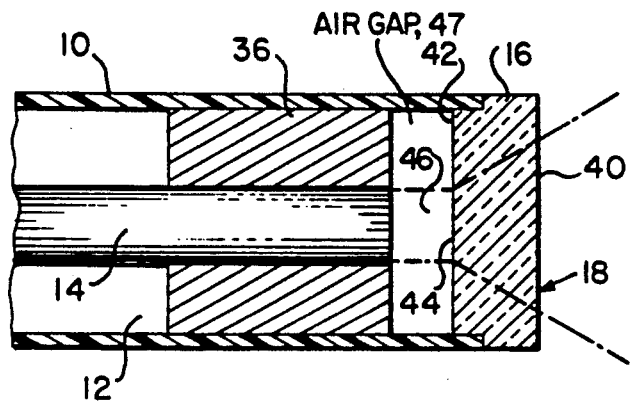
FIG. 2 is an enlarged and simplified cross-sectional view of the distal end of the laser catheter of FIG. 1.

A single optical fiber laser catheter is shown in FIG. 1. The catheter is formed from an elongated flexible tube 10 and, for example, may be extruded from an appropriate plastic material. The tube 10 has a lumen 12 for enclosing an optical fiber 14, as shown in FIG. 2. The distal end of the catheter is provided with a cap or catheter window 16. Radiant energy transmitted through the optical fiber 14 passes through the window 16 and is emitted in a controlled, predetermined pattern from an emission aperture 18 at the distal end of window 16.

At the proximal end of the catheter, flexible tubes 22 and 24 project from a fitting 20. The optical fiber 14 extends through fitting 20 and tube 22 to a connector 26. Connector 26 is adapted to be coupled to a source of radiant energy, such as a laser 27. The proximal end of the optical fiber 14 receives radiant energy from laser 27 and conducts it along its length to and through window 16. Tube 24 communicates through fitting 20 with the lumen 12 of the tube 10 and is provided with a conventional luer connector 28. The connector 28 provides a passageway for fluids or gases to flow through the lumen 12 in the tube 10. The tube 10 can be provided with apertures 30 for communication with the region of the blood vessel where the distal end of the catheter is located.

An enlarged and simplified cross-sectional view of the distal end portion of the catheter is shown in FIG. 2. The catheter window 16 is attached to the distal end of tube 10 by any convenient means, such as with an adhesive. The window 16 and the tube 10 preferably have the same outside diameter. The window 16 is substantially transparent to radiant energy in the wavelength range of laser 27. A cylindrical fiber holder 36 has a central bore for retaining optical fiber 14. The fiber holder 36 positions the optical fiber 14 in a fixed relationship to window 16. The catheter window 16 has a distal surface 40 and a proximal surface 42.

In accordance with one embodiment of the present invention, a transmission diffraction grating 44 is fabricated on the proximal surface 42 of window 16. The diffraction grating 44 is positioned on window 16 relative to optical fiber 14 so as to intercept a laser beam 46 emitted from the distal end of optical fiber 14. The purpose of the diffraction grating 44 is to modify the spatial distribution of laser beam 46. The diffraction grating 44, as described in more detail hereinafter, comprises a series of grooves in window 16. The laser beam 46 passes through the diffraction grating 44 and is bent or diffracted in different directions. The laser beam 46, after being diffracted by grating 44, diverges as it passes through window 16 and continues to diverge after it is emitted from the distal surface 40.

By appropriate selection of the grating 44 parameters and the axial thickness of window 16, the laser beam 46 can be expanded to the diameter of the catheter at surface 40 or in a plane spaced from and parallel to surface 40. When the laser beam 46 is expanded to the diameter of the catheter, the catheter can be utilized to form in an obstruction a hole having a diameter that is approximately equal to the diameter of the catheter, thereby enabling the catheter to be advanced through the hole. Thus, long obstructions can be removed by repetitively applying laser energy and advancing the catheter through the hole which is formed. Furthermore, by diverging the laser beam 46, the intensity of the laser beam rapidly drops in a distal direction below a level that is sufficient to remove or ablate tissue. Thus, the risk of vessel perforation is minimized.

The material just in front of the diffraction grating 44 must have a different refractive index than the material in which the grating is formed. In FIG. 1, the grating 44 is formed on catheter window 16. Since the optical fiber 14 may have a refractive index that is approximately the same as the refractive index of window 16, it is preferred to space the distal tip of optical fiber 14 from grating 44 by a short distance, typically on the order of about 25 micrometers. Thus, an air gap 47 is provided between the distal tip of the optical fiber 14 and window 16. It will be understood that materials other than air can be utilized to insure a difference in refractive indices at the surface of diffraction grating 44.

A laser catheter including multiple optical fibers and intended for use with a guidewire is illustrated in FIG. 3. The catheter is indicated by the reference numeral 60 with a guidewire 62 extending through the catheter. The catheter 60 has a main portion 68 with an outside diameter on the order of 1.5 mm. A branch fitting 70 is molded to the proximal end of main portion 68, and a plurality of tubes 72 extend proximally from fitting 70. Each of the tubes 72 is provided with a single optical fiber and has a connector 74 at its proximal end for connecting the optical fiber within each of the tubes 72 to a source of laser energy (not shown). The catheter 60 includes an additional flexible tube 76 which communicates with a lumen extending through the catheter through which the guidewire 62 is passed. The tube 76 has a fitting 78, which may be a luer connector, to enable the tube 76 to be connected to liquid infusion devices and/or pressure monitoring devices. The fitting 78 can be connected to a conventional Y-fitting to permit guidewire 62 to be controlled while also permitting liquid infusion and/or pressure monitoring.

The main portion 68 of catheter 60 typically includes an inner core or tube 80 surrounded by an outer tube 82. The inner tube 80 defines the lumen through which the guidewire 62 passes. The optical fibers extend through an annular region between inner tube 80 and outer tube 82. A generally cylindrical cap or catheter window 90 is attached to the distal end of outer tube 82.

Figure 4:
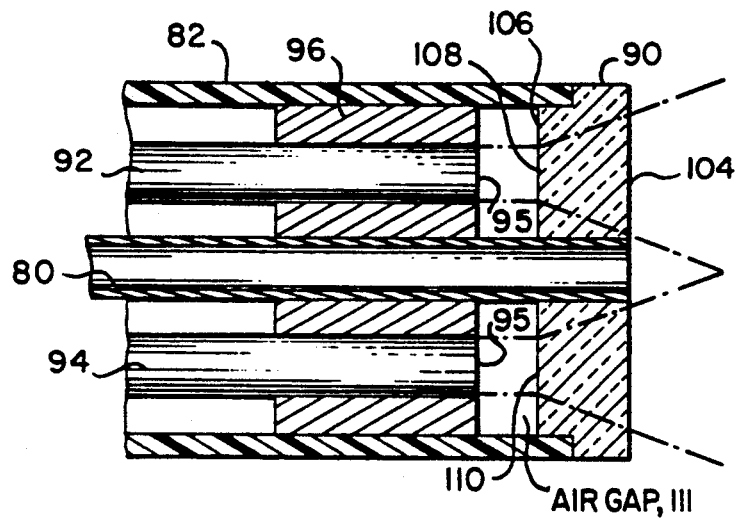
FIG. 4 is an enlarged and simplified cross-sectional view of the distal end of the laser catheter of FIG. 3.

A simplified cross-sectional view of the distal end of the catheter 60 is shown in FIG. 4. Optical fibers 92 and 94 extend through the annular region between inner tube 80 and outer tube 82 and are held in fixed positions relative to window 90 by a fiber holder 96. The fiber holder 96 includes circumferentially-spaced bores for retaining fibers 92 and 94 and a central bore for inner tube 80. The inner tube 80 extends through fiber holder 96 and is sealed to a central aperture in window 90. The inner tube 80 provides a lumen for passing the guidewire 62 through the distal end of the catheter 60. The catheter includes circumferentially-spaced optical fibers, two of which are illustrated as fibers 92 and 94. Each of the fibers 92 and 94 is held in a fixed and spaced relationship to window 90 by holder 96. Further details regarding the construction of a wire-guided laser catheter are disclosed in the aforementioned U.S. Pat. No. 4,850,351, which is hereby incorporated by reference.

The window 90 includes an annular distal emission surface 104 and an annular proximal surface 106. In accordance with another embodiment of the the present invention, transmission diffraction gratings 108 and 110 are formed on the proximal surface 106 of window 90 and are positioned so as to intercept laser beams emitted from optical fibers 92 and 94, respectively. The diffraction gratings can be fabricated as individual gratings or grating sections that are positioned on the proximal surface 106 to intercept each laser beam. Alternatively, a single diffraction grating of sufficient size to intercept the laser beams from all of the optical fibers can be fabricated on the proximal surface 106.

The diffraction gratings 108 and 110 diffract the laser beams emitted from optical fibers 92 and 94, thereby causing the beams to diverge as they pass through window 90 and to continue diverging after they are emitted from the distal surface 104. The distal tips of optical fibers 92 and 94 are spaced from the diffraction gratings 108 and 110 to provide a short air gap 111 proximal to diffraction gratings 108 and 110. The axial thickness of window 90 is selected in conjunction with the parameters of diffraction gratings 108 and 110 to provide a desired beam cross-section at the distal emission surface 104. Preferably, the composite beam formed by laser energy transmitted through each of the optical fibers has a sufficient diameter at distal surface 104 or in a plane spaced from distal surface 104 to form a hole through which catheter 60 can pass.

Figure 5:
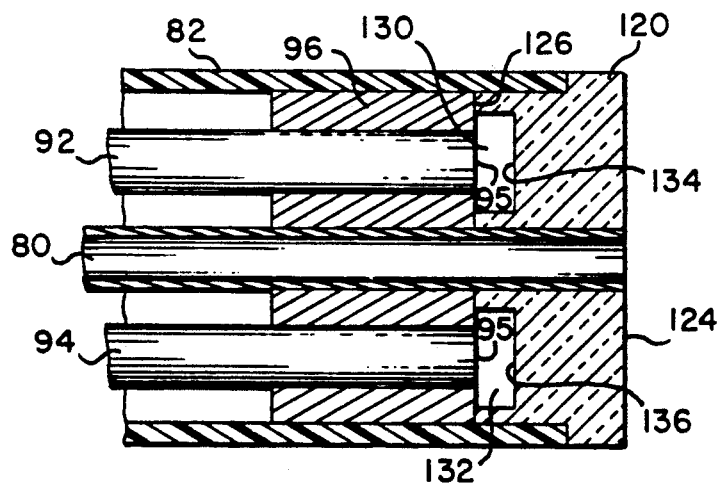
FIG. 5 is a cross-sectional view of an alternate embodiment of the distal end of the catheter of FIG. 3.

An embodiment of the catheter 60 having an alternate window configuration is shown in FIG. 5. Like elements have the same reference numerals in FIGS. 4 and 5. A generally cylindrical window 120 is attached to the distal end of outer tube 82. The optical fibers 92 and 94 are held in fixed positions relative to window 120 by fiber holder 96, as shown in FIG. 4 and described hereinabove. The inner tube 80 extends through fiber holder 96 and is sealed to a central aperture in window 120 to provide a lumen for passing the guidewire 62 through the distal end of the catheter.

Window 120 includes an annular distal emission surface 124 and an annular proximal surface 126. The window 120 typically has a larger axial dimension than the window 90 in FIG. 4. Recesses 130 and 132 are formed in proximal surface 126. The recesses 130 and 132 are aligned with optical fibers 92 and 94, respectively, and extend partway through window 120 in a distal direction. Diffraction gratings 134 and 136 are formed on end walls of recesses 130 and 132, respectively. The proximal surface 126 of window 120 preferably abuts against fiber holder 96, and the distal tips of optical fibers 92 and 94 are flush with the distal end of fiber holder 96. This configuration ensures that the diffraction gratings 134 and 136 are spaced from the distal tips of optical fibers 92 and 94 by a predetermined distance equal to the axial depth of the recesses 130, 132, without requiring special alignment procedures. The recesses can be formed as individual recesses aligned with each of the optical fibers. Alternatively, a single annular recess can be aligned with the circumferentially-spaced optical fibers. The diffraction gratings 134 and 136 operate in the manner described above to expand the laser beams emitted from optical fibers 92 and 94, respectively.

As discussed hereinabove, a transmission diffraction grating is formed on a surface of a catheter window at the distal end of a laser catheter to control the laser beam pattern, and more particularly, to expand the laser beam to a desired size and shape. The theory and techniques for fabricating diffraction gratings are well known in the art, as described in *Handbook of Diffraction Gratings, Ruled and Holographic*, Jobin Yvon Optical Systems, which is hereby incorporated by reference. The diffraction gratings utilized on laser catheter windows in accordance with the present invention can have a variety of configurations, depending on the desired beam pattern and the number of optical fibers utilized.

Figure 6A:
FIGS. 6A-6C illustrate diffraction grating patterns suitable for use in the present invention.

A conventional diffraction grating, as shown in FIG. 6A, includes a plurality of parallel grooves 140 formed in the surface of the window. The width and depth of the grooves and the spacing between grooves are a function of the laser wavelength. The groove parameters are selected to correspond to the laser wavelength being utilized and to the desired beam pattern. Parallel grooves produce bending of the beam perpendicular to the long dimension of the grooves 140. Thus, the beam is expanded in one dimension. A diffraction grating having uniform groove spacings produces a lobe pattern with maxima and minima at defined angles.

In a laser catheter, it is usually preferable to provide a generally uniform spatial distribution of laser energy intensity to insure uniform tissue removal within the beam pattern. A substantially uniform spatial distribution is provided by utilizing a diffraction grating with nonuniform groove spacings, preferably pseudo-random spacings. This configuration tends to smooth the lobe pattern and to produce a more uniform energy distribution. It is known that laser energy incident on biological tissue is scattered. The amount of scattering depends in part on the wavelength of the laser energy. In some cases, it may be desirable to use a diffraction grating having uniform groove spacings and to rely upon scattering to smooth intensity variations in the lobe pattern.

Figure 6B:
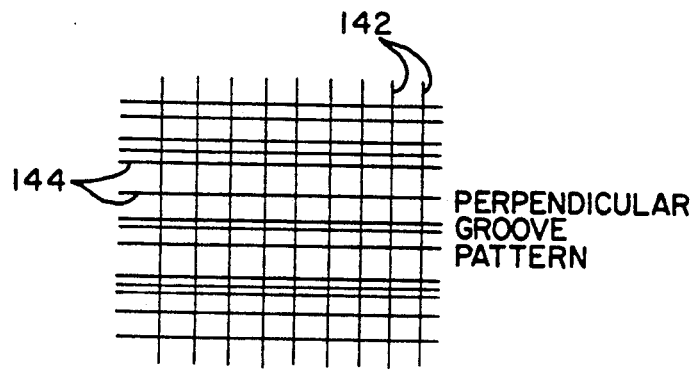
Figure 6C:
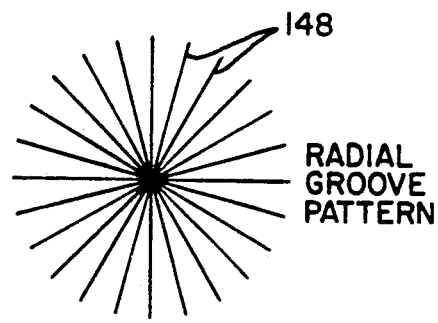

In order to provide beam expansion in two dimensions, a diffraction grating pattern as shown in FIG. 6B including a first set of parallel grooves 142 and a second set of parallel grooves 144 perpendicular to the first set of grooves 142 can be utilized. In FIG. 6B, vertical grooves 142 are illustrated as having uniform spacing, while horizontal grooves 144 are illustrated as having nonuniform spacing. As discussed above, the groove parameters are selected to correspond to the laser wavelength being utilized and to the desired beam pattern. Other suitable diffraction grating patterns include radial grooves 148 as shown in FIG. 6C which emanate from a central point, typically the axis of the catheter. Holographic diffraction gratings can also be utilized. Techniques for fabricating holographic diffraction gratings are described in the aforementioned Jobin Yvon Handbook.

In a preferred embodiment, the catheter window is silica, and the diffraction grating grooves are formed by conventional photolithographic or electron-beam lithography techniques and etching or ion milling. A technique for electron beam fabrication of holograms is described by S. M. Arnold in *Optical Engineering*, Vol. 24, No. 5, Sept./Oct. 1985, pp 803–807, which is hereby incorporated by reference. The disclosed technique can be utilized for fabrication of diffraction gratings with grooves having dimensions on the order of a few micrometers.

As discussed above, the diffraction grating is preferably formed on the proximal surface of the laser catheter window. This configuration protects the diffraction grating and permits expansion of the beam after it passes through the grating and before it exits from the distal emission surface of the catheter. In another embodiment, the diffraction grating is formed on the distal surface of the window. However, in this case, the distal end of the catheter must be spaced from the obstruction to be removed in order to provide sufficient distance for the beam to expand after it passes through the diffraction grating. In yet another embodiment, the diffraction grating is formed on the distal end surface of the optical fiber through which laser energy is directed. For example, with reference to FIGS. 4 and 5, transmission diffraction gratings are formed on the distal end surfaces 95 of optical fibers 92 and 94. The air gap between the distal ends of the optical fibers 92 and 94 and the respective windows provides the required difference in refractive indices.

In the embodiment wherein the diffraction grating is formed on the proximal surface of the window, the distal tip of the optical fiber is preferably separated from the diffraction grating by an air gap. However, another material can be utilized provided that the refractive index of the material differs from the refractive index of the window material in which the diffraction grating is formed. Although the diffraction grating is described herein as being formed directly on the catheter window, it can, within the scope of the present invention, be formed on a separate element positioned in the path of the laser beam that is emitted from the optical fiber.

It is known to differentiate plaque deposits from normal tissue by sensing fluorescence from the obstructed region. The fluorescence is typically stimulated by laser energy that is transmitted through the optical fiber or fibers. The fluorescence passes through the optical fiber or fibers in a reverse direction and is analyzed. The diffraction grating disclosed herein does not interfere with excitation or sensing of fluorescence. The wavelengths used for excitation of fluorescence and the wavelengths of fluorescence from tissue are typically shorter than the wavelength of the laser energy used for removal of obstructions. Since groove dimensions and groove spacings are a function of wavelength, a diffraction grating designed for use at the laser wavelength utilized for removal of obstructions is nearly transparent to the wavelengths associated with excitation and sensing of fluorescence. Furthermore, the spacing between the diffraction grating and the distal tip of the optical fiber is kept small, typically on the order of about 25 micrometers. Since the fluorescence passes in a reverse direction through the laser catheter window, any beam expansion caused by the diffraction grating must occur in the air gap between the diffraction grating and the distal tip of the optical fiber. When dimension of the air gap is small, very little expansion occurs, and most of the fluorescent energy is collected by the optical fiber.

Figure 7:
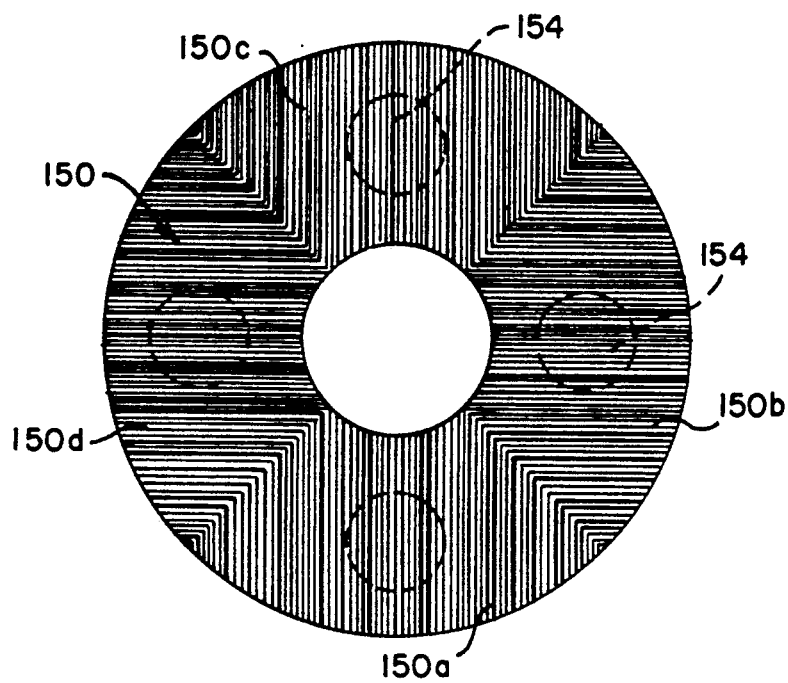
FIG. 7 illustrates an example of an annular diffraction grating pattern for use with four circumferentially-spaced optical fibers.
Figure 8:
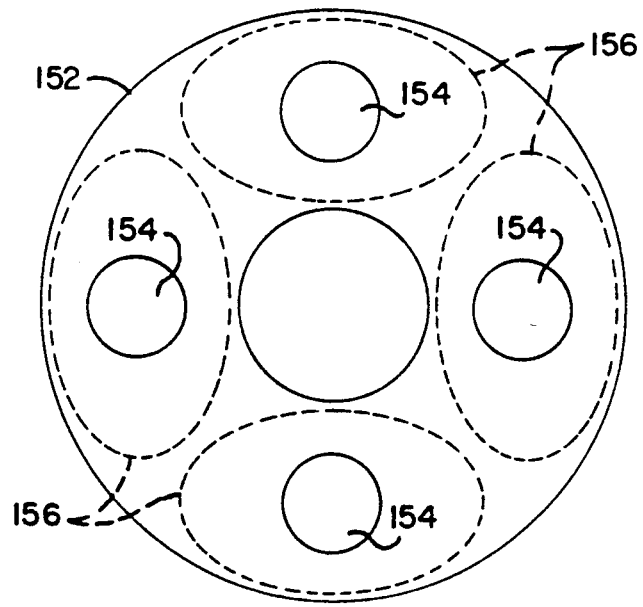
FIG. 8 is a schematic diagram showing an end view of an annular catheter window and laser beam cross-sections provided by the diffraction grating of FIG. 7.

An example of a diffraction grating 150 formed on an annular window of the type shown in FIG. 4 and described hereinabove is shown in enlarged form in FIG. 7. The diffraction grating 150 is configured for a catheter having four optical fibers 154 circumferentially-spaced around a central aperture. The diffraction grating 150 includes four grating sections 150a, 150b, 150c and 150d respectively aligned with optical fibers 154. Each of the grating sections 150a, 150b, 150c and 150d comprises parallel grooves having three micrometer features and pseudo-random spacings. The grating sections were formed on a fused silica window of 0.75 mm thickness. The beam pattern produced by a diffraction grating of the type shown in FIG. 7 is illustrated schematically in FIG. 8. An annular catheter window is represented by the reference numeral 152. The laser beams emitted by fibers 154 are expanded in a direction perpendicular to the grooves in the diffraction grating to provide elongated patterns 156.

When a diffraction grating is formed on a catheter window in accordance with the present invention, the axial window thickness can be on the order of 0.5 mm to 0.75 mm. By contrast, prior art catheter windows without diffraction gratings required an axial thickness on the order of 1 mm to 2 mm to provide sufficient beam divergence. A relatively thick catheter window undesirably increases the stiffness of the distal end of catheter. The diffraction grating permits a relatively thin catheter window to be used because the laser energy is diverged by the diffraction grating and expands to the required diameter over a shorter distance.

At a given laser wavelength, it is likely that the number of optical fibers required to remove obstructions can be reduced by utilization of the present invention. For example, at 2.1 micrometers the scattering of laser energy in tissue is relatively low, and seven optical fibers have been found necessary to form a 1.5 mm hole with a wire guided laser catheter. By use of a diffraction grating in accordance with the invention, the laser beam from each optical fiber is expanded, and a hole of a desired diameter can be formed with fewer optical fibers, thereby increasing the flexibility of the catheter. Additional advantages in reducing the number of optical fibers in a laser catheter include an increase in catheter reliability, a reduction in parts cost and an increase in manufacturing yield.

Referring again to FIG. 8, the optical fibers 154 emit laser beams which are circular in cross-section. The diffraction grating 150 modifies or shapes the laser beams to noncircular, elongated patterns 156. The noncircular beam patterns 156 are utilized to provide effective removal of obstructions, while minimizing the number of optical fibers in the catheter and minimizing the risk of damage to the blood vessel. Ideally, laser radiation should be emitted from the entire annular surface of catheter window 152. When the beam pattern is larger in diameter than window 152, the risk of damage to the blood vessel is increased. When the beam pattern is smaller in diameter than window 152 or does not otherwise fill the annular emission surface of window 152, tissue removal may be insufficient to pass the catheter.

It can be seen that the elongated beam patterns 156 fill the annular area of window 152 better than circular beam patterns. Expanded circular beam patterns would extend outside the area of window 152 and create a risk of vessel perforation. It is usually desirable that the beam patterns from each optical fiber 152 overlap at or near the distal surface of the window 152 to provide a continuous beam pattern.

Figure 9:
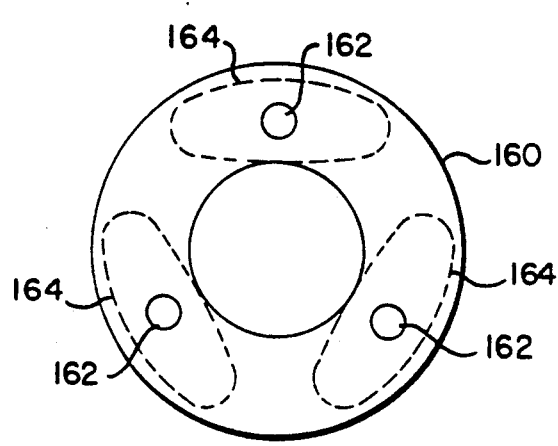
FIG. 9 is a schematic diagram showing an end view of an annular catheter window and laser beam cross-sections provided by three circumferentially-spaced optical fibers and a diffraction grating.

An example of the reduction in the number of optical fibers that is possible with the present invention is illustrated in FIG. 9, which illustrates the distal end of an annular catheter window 160 and three circumferentially-spaced optical fibers 162. The use of diffraction gratings as shown and described herein provides elongated beam patterns 164 By appropriate positioning of optical fibers 16 and selection of diffraction grating parameters, the beam patterns 164 can be made to nearly fill the emission surface of annular window 160.

Figure 10:
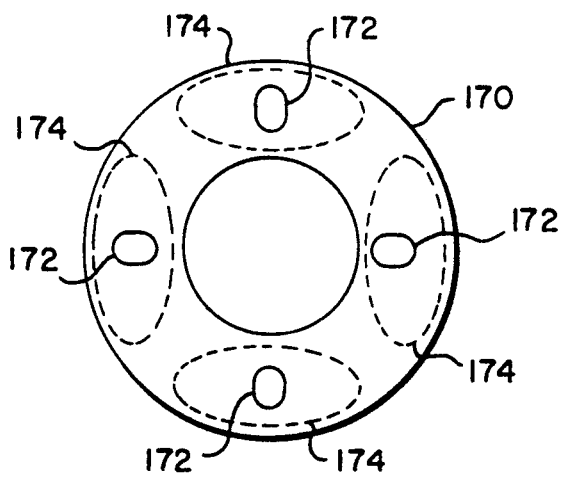
FIG. 10 is a schematic diagram showing an end view of an annular catheter window and laser beam cross-sections provided by four circumferentially-spaced noncircular optical fibers.

Another technique for providing noncircular beam patterns is illustrated in FIG. 10, which illustrates the distal end of a catheter window 170. Optical fibers 172 are circumferentially spaced with respect to the window 170. A portion of each optical fiber 172 near its distal end is deformed to have a noncircular, generally elliptical cross-section. Such elliptical fibers emit a laser beam having an elongated, noncircular pattern 174. As shown in FIG. 10, the long axis of the beam pattern 174 is perpendicular to the long axis of the fiber cross-section. Thus, in order to produce a generally annular composite beam pattern as shown in FIG. 10, the long axis of each fiber cross-section is oriented radially with respect to the catheter axis. Typically, about one inch near the distal end of each optical fiber 172 is deformed as shown. Techniques for deforming optical fibers in this manner are known in the art.

Figure 11:
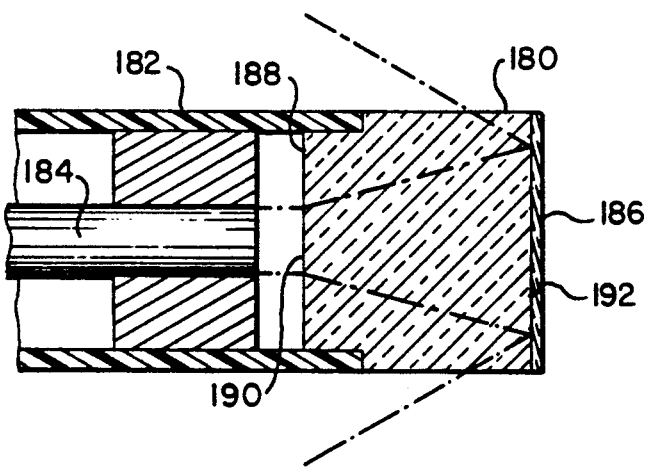
FIG. 11 is an enlarged and simplified cross-sectional view of an alternate embodiment of the distal end of the catheter of FIG. 1.

An alternate embodiment of the invention is illustrated in FIG. 11, which shows the distal end of a single optical fiber catheter. A window 180 is attached to the distal end of a catheter tube 182. An optical fiber 184 passes through a lumen in catheter tube 182 and directs laser energy through window 180. Window 180 has a distal surface 186 and a proximal surface 188. As described hereinabove, a diffraction grating 190 is formed on proximal surface 188 in alignment with the laser beam emitted from optical fiber 184. In the embodiment of FIG. 11, a reflecting layer 192 is formed on distal surface 186. The reflecting layer has a proximally-facing reflecting surface. A laser beam emitted from optical fiber 184 expands after passing through diffraction grating 190 and is then reflected in a reverse direction by the reflecting layer 192. The catheter thus emits laser energy in a generally proximal direction. A catheter which directs laser energy in a generally reverse direction is disclosed in U.S. Pat. No. 4,819,632 issued Apr. 11, 1989 to Davies, which is hereby incorporated by reference.

The present invention provides several advantages in comparison with prior art laser catheter constructions. The laser beam can be expanded, or diverged, without the use of an expensive and difficult to fabricate miniature lens. An area approximately equal in diameter to the diameter of the catheter can be removed with fewer optical fibers than was necessary in prior art configurations. By using fewer optical fibers, the flexibility of the catheter is increased. Furthermore, the axial dimension of a window necessary to provide an expanded beam is decreased, thereby reducing the axial length of the rigid distal tip of the catheter.

While there have been shown and described what are at present considered the preferred embodiments of the present invention, it will be obvious to those skilled in the art that various changes and modifications may be made therein without departing from the scope of the invention as defined by the appended claims.

What is claimed is:

1. A catheter for removing biological material from a body lumen with radiant energy, comprising:
   an elongated, flexible catheter body having a proximal end and a distal end and having a lumen for receiving a guidewire;
   a plurality of optical fibers extending through said catheter body, each of said optical fibers having a distal end, the distal ends of said optical fibers being circumferentially positioned around a longitudinal axis of said catheter body; and
   shaping means for modifying radiant energy directed through each of said optical fibers, said shaping means comprising means for producing for each of said optical fibers a spatial distribution pattern distally of said catheter having a cross section that is elongated in a circumferential direction relative to the longitudinal axis of said catheter body so that said distribution patterns together provide a radiation pattern distally of said catheter that is approximately annular, said shaping means comprising a section of each of said optical fibers near the distal end of said catheter body having an elliptical cross section in a plane perpendicular to a longitudinal axis of each of said optical fibers.

2. A catheter for removing biological material from a body lumen with radiant energy, comprising:
   an elongated catheter body having a proximal end and a distal end;
   at least one optical fiber extending through said catheter body from said proximal end to said distal end; and
   shaping means for modifying radiant energy directed through said at least one optical fiber, said shaping means comprising a section of said at least one optical fiber near the distal end of said catheter body having an oval cross section in a plane perpendicular to a longitudinal axis of the optical fiber, said shaping means providing an oval distribution pattern in a plane perpendicular to said catheter body and distally of said catheter.

3. A catheter as defined in claim 2 including plural optical fibers circumferentially positioned around a catheter axis and wherein said shaping means provides a distribution pattern for each of said optical fibers that is elongated in a circumferential direction.

4. A catheter for removing biological material with laser energy, comprising:
   an elongated, flexible catheter body having a proximal end and a distal end and having a lumen for receiving a guidewire;
   a plurality of optical fibers extending through said catheter body from said proximal end to said distal end, said optical fibers being circumferentially arranged in an annular array around a longitudinal axis of said catheter body, each of said optical fibers having a distal tip; and
   a window mounted at or near the distal end of said catheter body for transmitting laser energy carried through said optical fibers, said window having a transmission diffraction grating formed thereon, the distal tips of said optical fibers being mounted in alignment with said transmission diffraction grating such that laser energy directed through said optical fibers from the proximal end of said catheter body passes through said transmission diffraction grating, said transmission diffraction grating comprising means for producing for each of said optical fibers a spatial distribution pattern distally of said window having a cross section that is elongated in a circumferential direction relative to the longitudinal axis of said catheter body so that said distribution patterns together provide a radiation pattern distally of said window that is approximately annular.

5. A catheter as defined in claim 4 wherein said window has a distal surface and a proximal surface, said proximal surface having at least one recess formed therein, said at least one recess having an axial depth along a longitudinal axis of said catheter body and having an end wall with said transmission diffraction grating formed thereon.

6. A catheter as defined in claim 5 including means for spacing the distal tips of said optical fibers from said transmission diffraction grating by the axial depth of said at least one recess.

7. A catheter as defined in claim 4 wherein said window has a distal surface and a proximal surface, said transmission diffraction grating being formed on said proximal surface.

8. A catheter as defined in claim 7 wherein the distal tips of said optical fibers are spaced from the proximal surface of said window by an air gap.

9. A catheter as defined in claim 7 wherein said window has an axial thickness that is selected to provide a desired expansion of said radiant energy between said transmission diffraction grating and said distal surface.

10. A catheter as defined in claim 7 wherein said transmission diffraction grating comprises plural sections on said window, each of said sections being positioned to interrupt laser energy from one of said optical fibers, the transmission diffraction grating in each of said sections comprising multiple grooves, each of said sections having a groove orientation, the groove orientation for at least two of said sections being different.

11. A catheter as defined in claim 10 wherein said grooves are uniform in spacing.

12. A catheter as defined in claim 10 wherein said grooves are nonuniform in spacing.

13. A catheter as defined in claim 12 wherein said grooves have a pseudo-random spacing.

* * * * *